United States Patent
Hudak

(12) United States Patent (10) Patent No.: US 6,312,255 B1
(45) Date of Patent: Nov. 6, 2001

(54) ENDODONTIC ADAPTER FOR A SONIC SCALER

(76) Inventor: Kenneth Hudak, 748 Elma St., Akron, OH (US) 44310

( * ) Notice: Subject to any disclaimer, the term of this patent is extended or adjusted under 35 U.S.C. 154(b) by 0 days.

(21) Appl. No.: 09/498,458

(22) Filed: Feb. 4, 2000

(51) Int. Cl.⁷ ................................................. A61C 1/07
(52) U.S. Cl. ................................. 433/119; 433/127
(58) Field of Search ....................... 433/81, 102, 86, 433/119, 224, 118, 127

(56) References Cited

U.S. PATENT DOCUMENTS

| | | | |
|---|---|---|---|
| 4,229,168 | * | 10/1980 | Scholz ................ 433/102 |
| 4,818,229 | * | 4/1989 | Vasile ................ 433/81 |
| 4,992,048 | * | 2/1991 | Goof ................ 433/102 |

* cited by examiner

Primary Examiner—Todd E. Manahan
(74) Attorney, Agent, or Firm—John D. Gugliotta; Michael J. Corrigan

(57) ABSTRACT

The invention is an improved endodontic adapter for a sonic scaler consisting of a talon having a threaded end for insertion into the handle of the sonic scaler. A pair of downwardly pointed barbs protrude radially from the side of the adapter for receiving an elastic ligature which firmly holds the dental instrument such as file to the talon. The opposite end of the talon has a tapered shaft that receives an aperture drilled into the side of the dental instrument. The ligature is simply wrapped around the dental instrument on opposite sides of the talon and then the ends are wrapped around the downwardly pointing barbs.

2 Claims, 4 Drawing Sheets

ENDODONTIC ADAPTER FOR A SONIC SCALER

RELATED APPLICATIONS

The present invention was first described in Disclosure Document Number 463269 filed on Oct. 7, 1999. There are no previously filed, nor currently any co-pending applications, anywhere in the world.

BACKGROUND OF THE INVENTION

1. Field of the Invention

The present invention relates generally to dental instruments and, more particularly, to an endodontic adapter with a novel means for attaching a sonic dental instrument to the handle of a sonic periodontal scaler.

2. Description of the Related Art

The daily brushing and flossing of one's teeth is one of the most important hygiene functions that people perform. Failure to do so will inevitably cause tooth decay and gum disease requiring frequent trips to the dentist and expensive repair work. Despite even the noblest of efforts cavities can still appear and require a visit to the dentist. As most people know, a trip to the dentist is a very frightening experience. The dentist's office is filled with a variety of strange looking devices and equipment. The most infamous device is the dental drill which the dentist uses to drill out decayed tooth material from a tooth to make room for a filling. As most people will attest, this is a very unpleasant experience. Modern dentistry has yielded devices wherein the dental drill is mounted on the head of a sonic instrument. The vibrations of the sonic device are transmitted to the drill for removing decayed tooth material. A variety of other devices can also be mounted on the head of the sonic instrument such as files, reamers, broaches, spreaders, and pluggers each of which perform a different dental function. The present invention is an improved means and apparatus for attaching the dental instruments to the handle of the sonic scaler.

In the related art, there exists several patents for dental scalers and instruments attached to the scaler. Typically, these devices have a dental instrument attached to the head of the scaler. For instance, and of considerable relevance are U.S. Pat. No. 4,571,183 and 4,484,891 issued in the name of Nash which discloses an vibratory endodontic scaler with a dental file attached to the head of the scaler via a thumbscrew. However, a problem with this method of attachment occurs because the vibrations from the vibratory means loosens the thumbscrew and the dental instrument becomes loose. This can be disastrous when the instrument is in the patient's mouth. The remainder of the prior art utilizes similar methods to attach the dental instruments to the head of the vibratory means.

A search of the prior art did not disclose any patents that read directly on the claims of the instant invention; however, the following references were considered related:

| U.S. Pat. No. | Inventor | Issue Date |
| --- | --- | --- |
| 5,236,358 | Sieffert | Aug. 17, 1993 |
| 3,956,826 | Perdreaux, Jr. | |
| 3,589,012 | Perdreaux, Jr. | |
| RE 30,536 | Perdreaux, Jr. | Mar. 3, 1981 |
| 4,571,183 | Nash | Feb. 18, 1986 |
| 4,484,891 | Nash | Nov. 27, 1984 |
| 4,295,827 | Martin et al. | Oct. 20, 1981 |
| 4,850,867 | Senia et al. | Jul. 25, 1989 |
| 5,927,977 | Sale et al. | Jul. 27, 1999 |
| 5,419,703 | Warrin et al. | May 30, 1995 |

Consequently, a need has been felt for providing an improved apparatus and method of attaching dental instruments and the like to the head of a a sonic scaler. The development of the endodonic adapter for a sonic scaler fulfills this need.

SUMMARY OF THE INVENTION

It is therefore an object of the present invention to provide an improved adapter for holding a variety of dental instruments for a sonic scaler.

It is another object of the present invention to provide an improved means for attaching a dental instrument to the head of a sonic scaler.

It is yet another object of the present invention to provide a means for attaching a dental instrument to the head of a sonic scaler that will not loosen from the vibrations of the sonic scaler.

Briefly described according to one embodiment of the present invention, an improved endodontic adapter for a sonic scaler is provided consisting of a talon shaped mounting head having a threaded end for insertion into the handle of the sonic scaler. Located on the other end of the mounting head is a tapered shaft portion having a pair of downwardly pointed barbs which protrude radially from the side of tapered shaft portion. The pair of barbs are for receiving an elastic ligature which firmly holds a dental instrument such as an endodontic dental file to the adapter. The dental instruments used with the adapter have a specially formed aperture drilled radially into it so that the dental instrument may placed onto the tapered shaft portion. To secure the dental instrument to the adapter, the elastic ligature is simply wrapped around the dental instrument on opposite sides of the tapered shaft portion and then the ends of the elastic ligature are wrapped around the downwardly pointing pair of barbs. The dental instrument is now securely attached to the tapered shaft portion of the adapter.

BRIEF DESCRIPTION OF THE DRAWINGS

The advantages and features of the present invention will become better understood with reference to the following more detailed description and claims taken in conjunction with the accompanying drawings, in which like elements are identified with like symbols, and in which:

| LIST OF REFERENCE NUMBERS | |
|---|---|
| 5 | Sonic Unit |
| 6 | Tube |
| 7 | Handle |
| 10 | Endodonic Adapter |
| 15 | Mounting Head |
| 15a | Tapered Shaft Portion |
| 15b | Threaded Shaft |
| 15c | Barbs |
| 15d | Neck |
| 16 | Dental Instrument |
| 16a | Aperture |
| 20 | Elastic Ligature |

DESCRIPTION OF THE PREFERRED EMBODIMENTS

The best mode for carrying out the invention is presented in terms of its preferred embodiment, herein depicted within the Figures.

1. Detailed Description of the Figures

Figure 1:
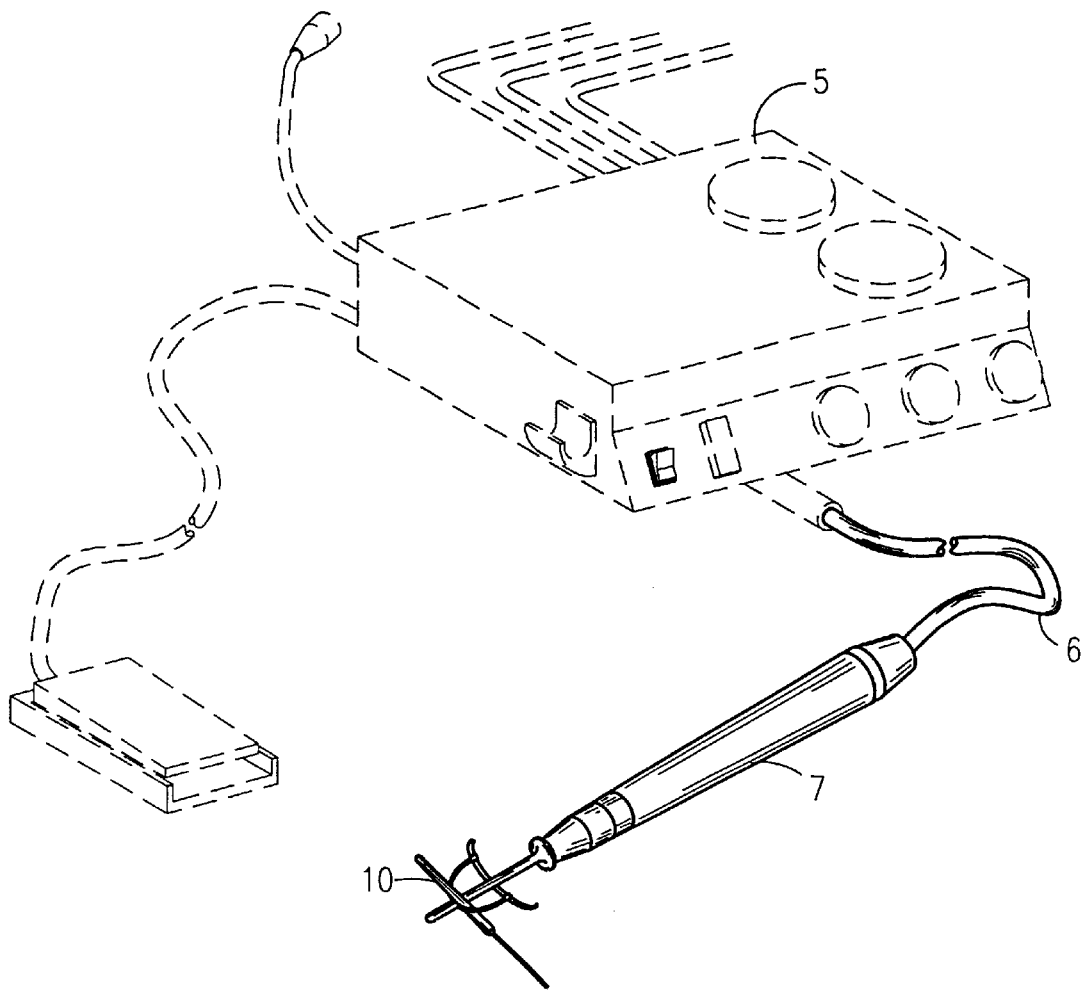
FIG. 1 is a perspective view of an endodonic adapter for a sonic scaler in the intended use, according to the preferred embodiment of the present invention.
Figure 2:
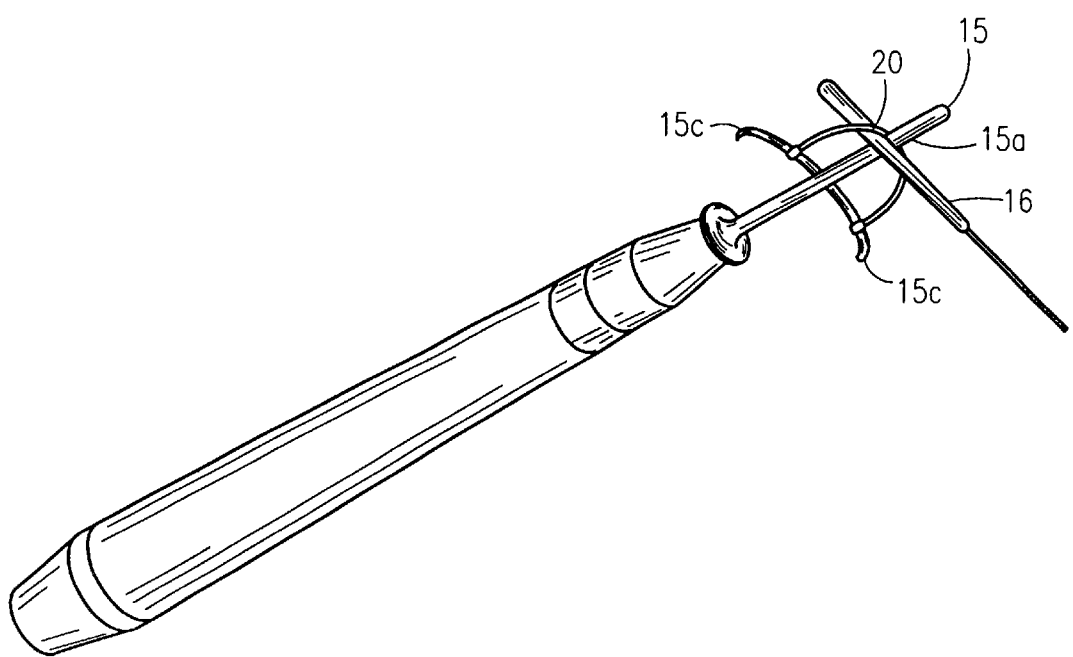
FIG. 2 is an exploded perspective view of an endodonic adapter for a sonic scaler, according to the preferred embodiment of the present invention.

Referring now to FIGS. 1 and 2, an endodonic adapter 10 for a sonic scaler is shown, according to the present invention, for attaching dental instruments to the handle 7 of a sonic scaler (as shown in FIG. 2). Typically, most modern dental offices have a sonic scaler (shown in FIG. 1) wherein an electrically powered base unit 5 generates sonic vibrations. The vibrations are transmitted by a tube 6 attached at one end to the base unit 5. The handle 7 is attached to the other end of the tube 6 for allowing the dentist to grip and manipulate the tube 6. A mounting head 15 is attached at the opposite end of the handle 7 wherein an assortment of dental instruments are attached for performing a variety of dental operations. The present invention is an improved mounting head 15 utilizing an elastic ligature 20 for securing the dental instrument 16 to the mounting head 15.

Figure 3:
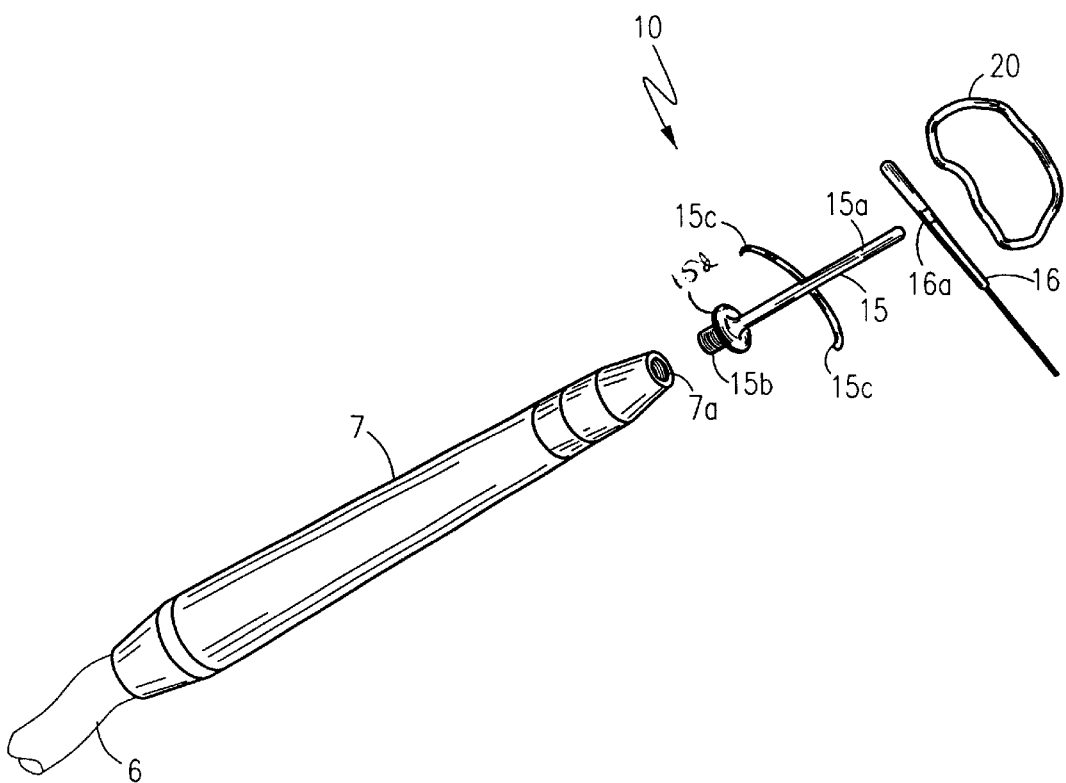
FIG. 3 is a front view of an endodonic adapter for a sonic scaler, according to the preferred embodiment of the present invention.

The present invention consists of a talon shaped mounting head 15 having a first end and a second end as shown in FIG. 3. The first end of the mounting head 15 is threaded, hereinafter referred to as threaded shaft 15b, for insertion into the handle 7 of the sonic scaler (not part of the disclosure). Mounting head 15 is simply screwed into the threaded cavity on the handle 7 of the sonic scaler 5. The second end of the mounting head 15 has a shaft portion 15a that tapers to a point. A pair of downwardly pointing barbs 15c emanate radially from opposite sides of tapered shaft portion 15a. An annular shaped neck 15d separates threaded shaft 15b and tapered shaft portion 15a. Mounting head 15 and pair of barbs 15c are formed from a material such as stainless steel, rubber, or plastic but the materials are only meant as suggestions and in no way are limiting. Tapered shaft portion 15a is for receiving an aperture 16a drilled radially into any one of a number of common dental instruments such as drills, files, reamers, shapers, spreaders, and pluggers, hereinafter denoted as element 16 in the figures. The dental instrument 16 held securely to tapereed shaft portion 15a by an elastic ligature 20 wrapped around dental instrument 16 on opposite sides of shaft portion 15a. The ends of ligature 20 are wrapped then secured around pair of barbs 15d. Elastic ligature 20 is typical ligatures found in dental office and any ligature of roughly the right size can be used. Alternately, any type of elastic or rubber band may be substituted as long as suitable guarantees of sterility are observed.

Figure 4:
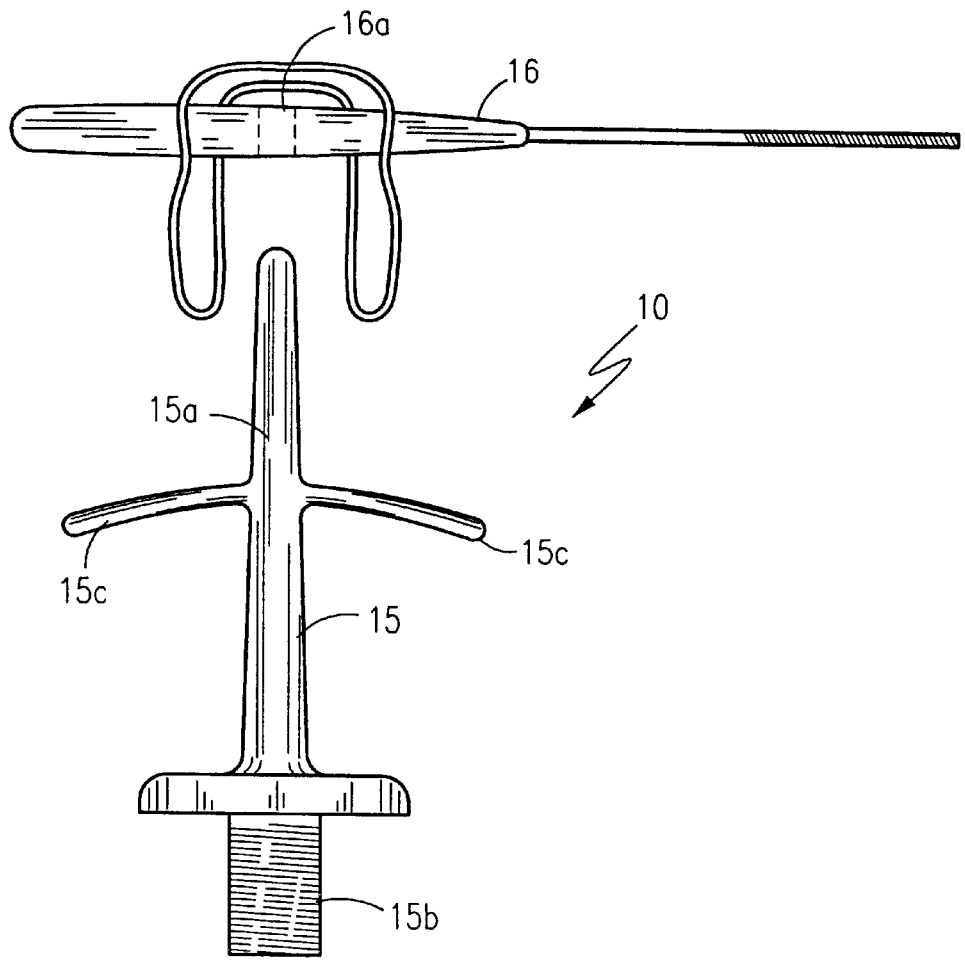
FIG. 4 is a top view of an endodonic adapter for a sonic scaler, according to the preferred embodiment of the present invention.
Figure 5:
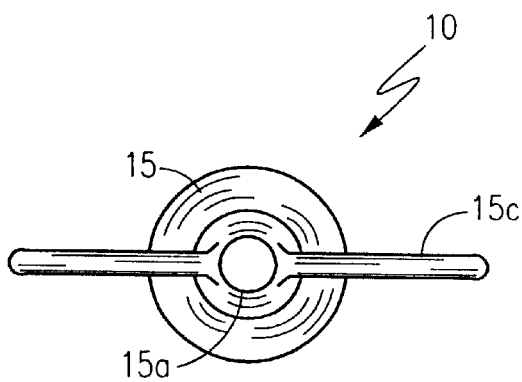

FIGS. 3 and 4 show various other views of the endodontic adapter 10 showing the location of pair of barbs 15d emanating radially from shaft portion 15a.

2. Operation of the Preferred Embodiment

To use the present invention, an aperture drilled into the side of an endodontic dental instrument such as a file, drill, reamer, broach, or plugger is inserted onto a specially formed shaft on an upper portion of the talon shaped mounting head. The dental instrument is held securely thereto by an elastic ligature wrapped around it on opposite sides of the shaft. The ligature is then secured by wrapping the ends of the ligature on a pair of downwardly pointing barbs protruding from opposite sides of the tapered shaft portion. The bottom portion of the mounting head has a threaded shaft portion for insertion into the handle of the endodonic sonic scaler. The base unit is then turned on and the dental instrument inserted into the mouth of the patient. If another instrument is needed, it can quickly and easily be changed by pulling the elastic ligature from the barbs and removing the old dental instrument.

The foregoing description is included to illustrate the operation of the preferred embodiment and is not meant to limit the scope of the invention. The scope of the invention is to be limited only by the following claims.

What is claimed is:

1. An endodontic adapter for mounting an endodontic dental instrument onto the handle of a endodontic sonic scaler, comprised of:

a mounting head, said mounting head having a first end and a second end, is talon shaped, and has a threaded shaft at said first end for insertion into the handle of the sonic scaler, and wherein said second end has a tapered shaft portion;

an annular neck, said annular neck separating said threaded shaft from said tapered shaft portion;

a pair barbs, said pair of barbs pointing downwardly and emanating radially from opposite sides of said tapered shaft portion;

a endodontic dental instrument selected the group consisting of drills, files, reamers, shapers, spreaders, and pluggers wherein said dental instrument has an aperture drilled radially into it for placing said dental instrument onto said tapered shaft portion of said mounting head;

an elastic ligature having two ends, wherein said elastic ligature is for securing said dental instrument to said tapered shaft portion by wrapping said elastic ligature around said dental instrument on opposite sides of said tapered shaft portion and wrapping said ends of said elastic ligature around said pair of barbs.

2. The endodontic adapter for mounting an endodontic dental instrument onto the handle of a endodontic sonic scaler of claim 1, wherein said mounting head and said pair of barbs are made from a material from the group comprising stainless steel, plastic, or rubber.

* * * * *